United States Patent
Thornton

Patent Number: 5,564,433
Date of Patent: Oct. 15, 1996

[54] METHOD FOR THE DISPLAY, ANALYSIS, CLASSIFICATION, AND CORRELATION OF ELECTRICAL BRAIN FUNCTION POTENTIALS

[76] Inventor: Kirtley E. Thornton, 24 Highland Ave., Metuchen, N.J. 08840

[21] Appl. No.: 359,183

[22] Filed: Dec. 19, 1994

[51] Int. Cl.$^6$ .................................................. A61B 5/04
[52] U.S. Cl. ........................... 128/731; 128/732; 128/644
[58] Field of Search .................................. 128/644, 731, 128/732, 697

[56] References Cited

U.S. PATENT DOCUMENTS

| | | |
|---|---|---|
| 3,707,147 | 12/1972 | Sellers . |
| 3,755,922 | 9/1973 | Clynes . |
| 4,332,566 | 6/1982 | Mazeski et al. . |
| 4,688,105 | 8/1987 | Bloch . |
| 4,755,889 | 7/1988 | Schwartz . |
| 4,863,384 | 9/1989 | Slade . |
| 4,932,416 | 6/1990 | Rosenfeld . |
| 5,119,816 | 6/1992 | Gevins .................................. 128/644 |
| 5,137,027 | 8/1992 | Rosenfeld . |
| 5,406,956 | 4/1995 | Farwell .................................. 128/731 |

Primary Examiner—Angela D. Sykes
Assistant Examiner—Stephen Huane
Attorney, Agent, or Firm—Abdallah & Muckelroy

[57] ABSTRACT

An actuarial method for statistically determining the probable truth or falsity of a statement concerning a human subject and whether responses or statements made by the subject precede either a knowing representation by the subject of a truth or a lie. The method enables the correlation of a video image of a human subject, including mannerisms of the human subject, a selected plurality of eclectroencephalographic signals gathered from a plurality of electrodes located at specific points on the head of the subject, and a simultaneous detection or display of the subject's responses from a single video monitor combined with a computer analysis of the electroencephalographs to determine the subject's knowledge regarding a fact, a personal experience, and/or the truth or falsity of a particular statement by using a set of regression equations which establish before-truth, before-lie, during-truth, and during-lie base actuarial profiles for correlation and comparative analysis via computer. A system provides remote audio communication between the human subject and an examiner, a computer for analyzing electroencephalographic responses of the subject and comparing same with the base acturial profiles is provided and connected for receiving and sending a video image of the subjects face onto a portion of a monitor while simultaneously processing, sending and displaying the plurality of brain electrical waves on a another portion of the monitor. The electrical signals from the subject's brain are acquired using a novel disposable elastic skull cap with 19 electrodes pre-inserted in the cap in pre-selected positions. The computer digitizes each electrical signal over a unit of time and compares digitized signals for different epochs of times with the signals generated from selected epochs serving as actuarial base line signals.

12 Claims, 3 Drawing Sheets

METHOD FOR THE DISPLAY, ANALYSIS, CLASSIFICATION, AND CORRELATION OF ELECTRICAL BRAIN FUNCTION POTENTIALS

BACKGROUND OF THE INVENTION

1. Field of the Invention

The present invention relates to an improved method for measuring, determining, recording and correlating event-related electrical brain potentials ("ERP") with the use of whole skull electroencephalography, to a novel disposable electrode cap, to a novel computer system arrangement and more particularly to a method of measuring and determining a large number of meaningful brain electrical potential changes in response to a continuously presented and varied specific verbal stimulus or verbal stimuli interspersed with non-significant verbal stimuli comprising known truths or true statements and false statements concerning the subject to establish an actuarial or historical personal base line for use within a predetermined time period and analyzing the measured ERP responses against the personal base line established from the related ERP data established from known stimuli to determine the probable truth or falsity of either a non-verbal (e.g. manual) response or verbal response to at least one specific stimulus in the form of a verbal query within the predetermined time period, using a computer.

2. Description of the Prior Art

The history of lie detection by psychophysiological methods has been fraught with problems of flawed human judgment, unreliability and frequent invalidity.

Medical records from the Hindus dated 900 B.C. were the first to note the use of blushing (facial vasodilation) in the detection of guilt. The earliest most impressive use was in the case of Eristratus, physician to Alexander the Great, who determined by use of the "tumultuous rhythm" of the heart that the crown prince of the Seleucid court in Syria was guilty of sexual relationship with his recently obtained stepmother. Months later, a female was born. Hugo Munsterberg in a published work dated 1908 was the first well known psychologist to give approval to the technique developed by one of his students, who reported a 96% accuracy rate using blood pressure as the single measure.

There have been two main techniques in the lie detection problem. The relevant/irrelevant technique ("RIT") asks subjects questions related to the crime and neutral questions that refer to everyday events. The problem with this approach is that if one is asked about a murder, it is not uncommon to achieve a greater physiological reactivity just to the question, which is irrelevant to the guilt of the subject.

To improve the RIT method, in 1947 Reid developed the control question technique ("CQT"). In this technique the control question is constructed to have greater emotional impact than the relevant question. Thus the subject might be asked "Did you ever do anything you were ashamed of?" Backster reported in a 1962 publication that he developed a quantification of this method by having the examiner rate each physiological measure on a scale of 1–3 for the control/relevant questions, depending upon the relative magnitudes of the responses to the questions. Thus, degrees of how much a subject falls in the respective category can be established.

Dr. D. Raskin et al. later developed computerized scoring for the CQT, taking it out of the hands of human judgment. Some approaches to the CQT employ a "truth control" test or "the guilt complex test" during which the subject is questioned regarding an additional crime. The questions are formulated the same and the underlying assumption by the subject that he is a suspect for both crimes must be met for this method to be effective and valid, which poses a special problem for the police in the beginning of an investigation.

This last approach was developed by Lykken in 1960. It is called the guilty knowledge test or concealed information test (herein after "GKT"). In this approach indirect questions are posed to the subject which are directed towards information that only the guilty subject would know. For example, "Was she wearing a black dress that night?" A multiple choice format has been employed in this approach. For example, "Was she wearing a red dress that night?" By focusing on several aspects of the crime and repetition of the questioning, false positives can be avoided. The use of the GKT has been supported in the published research on the subject. In Japan, the use of the GKT is the preferred technique, but it has not been widely used in the U.S.

In reviewing the results of published research in this area, noteworthy is a work by Ben-Shakhar in 1990 which reported that the studies employing the CQT resulted in average correct classification of guilty subjects between 80% and 84% in simulated and field studies, respectively. Among innocent subjects, the correct classification was 63%–72%, respectively. The GKT, on the other hand, averaged across 10 studies a 84% hit rate for the guilty subjects and 94% hit rate for those simulating innocence.

Published works by Gustafson and Orne in 1965 demonstrated that by asking the subjects to respond "no" to all the questions they were able to obtain a higher identification rate than the control group which were instructed to respond with a free association. A third group was instructed not to respond. The researchers were able to obtain significantly higher than chance hit rates for this silent group and "no" group. Further research published by Horneman and O'Gorman in 1985 and by Elaad and Ben-Shakhar in 1989 has validated this effect of silence during the question period.

Additional published research by Cutrow et al. (1972) and also previously indicated by Thackray and Orne (1968) validated the use of several measures in increasing accuracy of prediction. They found that although galvanic skin response ("GSR") was the single best predictor, the combined score using six measures produced more effective results. The novel invention accurately and effectively extends this discovery a thousandfold and combines it with certain other novel procedures to substantially improve results.

Electroencephalography ("EEG") is a method of recording brain waves of an individual which are generated by the action potentials of neurons residing in the cortex of the brain. In today's standard 1020 systems, 19 electrodes are positioned on the scalp covering the skull with conductive paste while two other electrodes are attached to a person's ears as reference points. The paste has several drawbacks. Sometimes, conduction is poor, intermittent, or impaired.

Spectral analysis of these brain waves is performed when each electrical potential signal is displayed versus a unit of time as representative of a particular brain wave detected by an electrode. Each brain wave from each electrode is amplified in voltage the same percentage. The wavelengths or frequencies in each brain wave are measured and then a signal uniquely representing each frequency of the brain wave is sent to a computer for sorting of the different frequencies of which the signal is composed. The range as measured in Hertz (cycles per second) is defined by the computer and analyzed in terms of absolute microvolts of electrical potential, relative potentials, coherence values (the similarity of the signal between two points on the scalp), ratio symmetry (the relationship between two points in terms of a particular bandwidth), peak amplitude (the peak microvolts of a particular bandwidth), peak frequency (the highest frequency of a particular bandwidth), and phase (the time lag difference between the signals at two different points on the scalp).

An epoch is the time it takes the computer to record a measurement of all of the signals from each of the electrodes. The sampling rate of the computer is the number of times it records measurements from the electrodes each second. Thus, the sampling rate of the computer determines the length of each epoch. For example, if the sampling rate is set at 128, then the maximum hertz range one is able to analyze is the sampling rate divided by 4, i.e., 32 hertz. Hertz is defined as the number of waves per second emanating from an electrode. If the sampling rate is set at 512, then one is able to analyze frequencies up to the 128 Hertz range. Different Hertz ranges have been associated with different mental states. For example, the alpha range of 8 to 12 or 13 Hertz has been associated with a relaxed state of mind. The Beta band of 12 or 13 to 128 has been associated with the working, problem solving brain.

Simultaneous video and EEG recording has been employed to assess for faking of seizures, etc. and for other pathology determinations.

An electroencephalograph ("EEG") is a device which measures and records brain wave activity by sensing spontaneous electrical potential of a person's scalp, cortex, or cerebrum at various sites. Each EEG channel corresponds to a particular electrode combination attached to the patient. The sensed EEG potential at each channel is amplified by a differential amplifier, and amplifier output signal is typically used to control movement of the recording pen of a polygraph. The EEG record is a long strip of polygraph paper containing a wave form for each EEG channel. The polygraph paper is driven at a predetermined rate (e.g., 30 millimeters per second) and is marked to represent predetermined time increments.

EEG signals exhibit different frequencies depending upon varying activity. The EEG signal frequencies are classified into four basic frequency bands, which generally referred to as "Delta" (0 to 4 Hertz); "Theta" (4 to less than a 8 Hertz); "Alpha" (8–13 Hertz); "Beta" (greater than 13 Hertz). One determines the predominant frequency of a particular channel during a particular time period by measuring the period of the EEG signal wave form shown on EEG record. The EEG signal wave form typically includes multiple frequency components. EEG outputs can be driven by specific extrinsic or endogenous events. For example, a regularly occurring stimulus will elicit a series of waves each time it is presented. The entire series is referred to as an event-related potential (ERP).

Besides the frequency of the EEG or ERP wave forms, the amplitude is measured. Significance has been established when large amplitudes of brain waves occur at about 300 ms or more after the eliciting event. There is evidence to suggest that this P300 wave process is invoked when the updating, or "refreshing", representations in working memory is required. Donchin, *Psychophysiology*. Vol. 18, 493–513 (1981); Fabiani, Karis, and Donchin, *Psychophysiology*, Vol. 22, 588–589 (1981).

Large P300's are elicited by rare or unexpected events, when they are relevant to the task the subject is performing. Such events may lead to restructuring or updating of working memory, and this activity is part of the ongoing process of maintaining accurate schemas of the environment. The updating process may lead to an "activation" of the representation, or to the "marking" of some attribute of the event that was crucial in determining the updating process. This restructuring of the representation of an event is assumed to facilitate the subsequent recall of the event, by providing valuable retrieval cues, so that the greater the restructuring that follows an individual event, the higher the probability of later recalling that event. If P300 amplitude represents the degree of restructuring in working memory, then P300 amplitude should also predict later recall. Fabriani, Karis and Donchin, *Psychophysiology*, Vol. 23, 298–308 (1986).

In view of the current knowledge of the frequency and amplitude of brain wave forms and with the advent of widespread use of the computer in behavioral neuroscience, the analysis of data has become easier. Oftentimes, it is desirable to have an objective method of determining whether or not a person has seen or otherwise has knowledge of a particular item, such as a weapon, a crime scene configuration, a secret document, a stolen object, or another person's face. Such knowledge is what is taught by prior art procedures and devices used in guilty knowledge tests, a sub-category of procedures used in physiological detection of deception ("lie detection").

The present invention is directed to a reliable, valid easy-to-use and accurate procedure for determining guilty or other knowledge on the part of an individual whose simple verbal report may be unreliable for various reasons. If a discreet stimulus, for example, a sound, a light flash, a tap-is presented to a human, his electroencephalogram shows a series of time-locked responses called event related potentials (ERP).

It was shown in the 1960's that if a subject is presented with a series of stimuli of two types, e.g., a high tone and a low tone, and if either of those tones is presented in 20 of 100 trials (with the remaining 80 trials containing the other tone), the rare stimulus will evoke a large ERP retorted to as "P3" or the previously described P300 brain wave. In this so-called "oddball" paradigm, it is known that P3 amplitude varies with rarity. Sutton, S. et al., *Science*. 150, 1187–1188, (1965).

in the 1970's and thereafter, other workers reported that P3 is evoked by words (or pictures) previously seen by a subject when presented in a word (or picture) series which also includes novel words (or pictures) which fail to evoke P3. Karis, D. et al., *Cognitive Psychology*, vol. 16, 177–216; Neville, H. et al., *Proc. Nat Ac. Sci.* U.S.A., vol. 79, 2121–2123, (1982).

The present invention also relates to a novel method which utilizes both the aforementioned effects so that one can tell by objective ERP inspection alone which of the presented stimuli has previously been seen by the subject or loaded into the subject's neural memory. The invention further relates to an apparatus which provides means for a repeated presentation of the significant stimulus and means for analyzing the ERP responses to determine the significance of all gathered responses. The prior art only used P3 responses in an "odd-ball" procedure with simple auditory stimuli, e.g. high tones and low tones, that were presented singly to subjects and whatever tone was presented less often evoked a P3 response. Pritchard, et al., *Psychophysiology*, Vol. 23, No. 2, 166–172 (1986).

The prior art also utilizes the "odd-ball" paradigm in which the stimuli is a simple visual flash differing in brightness. Johnson, Jr. *Annuals of the N.Y. Acad. of Sci.* Vol. 425, pages 223–230 (1984). Like Pritchard, other studies utilized P3 responses relating them to memory updating processes, expectancy processes, surprise, and so forth. None of the prior art articles disclose the odd-ball procedure with repeated, meaningful word stimuli in the context to be utilized to detect guilty knowledge or other recognition processes.

In the paper by Fabiani, et al. *Psychophysiology*, Vol. 23, pp. 298–308 (1986) and Neville, et al. supra, verbal, meaningful stimuli is used in a variant kind of "odd-ball", paradigm bearing on recognition memory. However, this teaching differs greatly from the present invention. Three or the most notable aspects are as follows: (a) These studies were not and could not be configured as field-relevant deception detection paradigms, because both novel and previously seen words (or pictures) in these studies were never repeated within the EEG run; (b) the average ERP to previously seen words (or pictures) was an average of responses to a series of all different words (or pictures); and (c) the average ERP to novel words (or picture) was likewise an average of responses to all different novel words (or pictures). This kind of paradigm is specifically unsuited to the real criminal-type lie detection investigations to which this invention is directed since it is usually a single item (the murder weapon, the stolen item, the classified document) which is involved in a real crime.

The Fabiani and Neville, reports are directed at and tailored to scientific elucidation of memory processes. In these studies, the repetition of words is avoided for fear of engaging habituation processes which would tend to reduce P3 effects. In the present invention, the "odd-ball" item is "odd ball" by virtue of its familiarity (e.g., as guilty knowledge). The stimuli are all meaningful words, and they are presented in the simplest possible, basic "odd-ball" design. There are other studies in the literature which do not use quasi verbal stimuli which are repeatedly presented. A review of the literature reveals that these studies are not using "odd-ball" paradigms, and are, in fact, studying memory processes with extremely complicated procedures tailored to these purposes: For example, Gomer et al., *Physio. Psych*, Vol. 4 (1) pp. 61–65 1976), (1976 Ford, et al., *Elect. Clin. Neuroph.* 47:450–459 (1979 Kramer et al. *Psychophysiology*, Vol. 23 No. 1, 33–47 (1986) and Adam and Collins, *Elec. Clin. Neurol.* 44: 147–156 (1978), all use a "go-no go" or pattern matching paradigms. A set of letters or numbers is memorized and then the subject is given a trial series in which he decides whether ("go") or not ("no go") a memorized target stimulus is presented.

The present invention requires but one series of trials; others use several sets. The present invention requires no feed-back whereas the prior art methods do. The prior art methods use warning tones whereas the present invention does not. It is notable that typically the prior art reports P3 responses to both target and non-target stimuli. Although target effects are often reported to be bigger, unambiguous use of P3 responses in field investigations of deception requires the kind of virtually all-or-none results that are seen in the present invention. Further, the prior art studies use simple stimuli, digits or letters, rather than meaningful words.

The main intent of most prior art methods was elucidation of memory retrieval processes. These methods focused on P3 latency rather than on amplitude. Instruments have been used to determine psychological stress, for example, the apparatus described in U.S. Pat. No. 2,944,542 relates to a blood pressure measuring device that indicates variations in the velocity of pulse wave thereby indicating a change in emotional state. U.S. Pat. No. 3,971,034 describes a method and apparatus for identifying psychological stress by converting oral impulses into electrical signals and recording, observing and analyzing those signals.

U.S. Pat. No. 3,893,450 relates to method and apparatus for examining brain wave form by providing stimuli such as light and determining the characteristic of a mathematically determinable point in the brain wave forms of the subject. U.S. Pat. No. 4,188,956 relates to a method of acquiring and compressing neurometric test data by means of a digital computer system. U.S. Pat. No. 4,579,125 relates to a method for processing analog EEG signals to provide an indication of cerebral activity. None of the teachings of the references, however, have been used for the combination of a method to determine P3 responses from repeatedly presented stimulus interspersed with no significant stimuli to obtain results directed towards detection and control question testing.

More recently, U.S. Pat. No. 4,932,416 issued on Jun. 12, 1990 to Rosenfeld for a method for recording and analyzing event-related potentials (ERP), and their respective P300 brain wave responses from a repeatedly presented guilty knowledge or control question stimulus interspersed with non-significant stimuli. A computer is utilized to interpret and analyze the responses for guilty knowledge relating these responses to the responses to control questions. An improvement was patented by Rosenfeld in U.S. Pat. No. 5,137,027 on Aug. 11, 1992 wherein the ERP's concurrently generated by a repeated paradigm are encephalographically sensed and analyzed for P3 content and the P3 waves generated and compared via computer. Based on selected criteria, a conclusion regarding actual prior act performance is made. Computer means are utilized to regulate the paradigm presentation and to interpret and analyze the P3 responses.

SUMMARY OF THE INVENTION

A method for determining the existence or extent of prior undisclosed cognition in a human subject of facts, perceived information such as personal knowledge of prior social behavior, acts, pain, or the like (including awareness of guilt), and/or the extent or level such cognition present in a human subject by using a large universe of objective criteria, electrical brain responses, created from known credible responses previously provided by the subject and recorded and analyzed to directly formulate the objective criteria during the examination period for use with data obtained within the examination period. The apparatus and method presents a system for collecting EEG signals using a novel disposable elastic skull cap adapted with metal hyperdermic electrodes are attached to the subject with a conducting gel. The electrodes contain an electrically conducting gel pre-placed therein for assuring reliable electrical contacts.

DESCRIPTION OF THE PREFERRED EMBODIMENT

In the preferred method of the novel invention, a plurality of stories, for example five, is obtained regarding a like plurality of events in a human subject's life. The subject is first asked to tell the truth about these events. Thereafter the subject is asked to lie or deliberately falsify his verbal description of these events. Each account by the subject occurs over a measured time period. The time period is divided into a fixed number of epochs by the examiner for analysis and epoch classification of the subject's epochal responses by a computer. The subject's account is classified as follows: (1) Before a known false statement or lie; (2) before a known true statement; (3) during a known false statement or lie; and (4) during a known true statement. During this period, the subject's electroencephalographic waves generated from 19 electrodes attached to the subject's skull are digitized. The nineteen electrodes are placed and arranged in a novel manner discovered to provide data which can be more accurately classified into one of each of the four categories.

The novel electrode cap positions are modified from those presented by the standard elastic cap from Electro-Cap International, for example, which employ the standard 10–20 positions. The positions for FP1, FP2, F7, F8, and CZ retain their normal positions and names in the standard manner as defined by the 10–20 system and its standard nomenclature. The standard FZ position is employed but renamed PZ. The standard T5 and T6 positions are employed but renamed as O1 and O2, respectively. The remaining 12 positions are relocated to maximize the number of frontal locations for these 12 electrodes. The remaining standard nomenclature is employed for these 12 positions relocated to the frontal lobe. The standard nomenclature, at this point, does not refer to the standard locations for these 12 electrodes. If a horizontal line is drawn between the standard FP1 and FP2 positions and the midpoint of that line is taken and a vertical line is drawn to the standard FZ position (now labeled PZ) and that vertical line is trisected into three equal spaces, this creates two additional locations: The bottom location is now labeled FZ, the second or central position is used as the ground location for the ground electrode, and the third position is designated the PZ position (in the 10–20 it is the standard FZ location). To obtain the locations C3 and F3 (old nomenclature, new positions), a line is drawn between the newly created FZ position and the F7 (standard location, standard nomenclature) and divided into three equal spaces with points for locating electrodes at the end of each space. As one moves from the FZ position to the F7 position on the side, the first point is labeled C3 and the second point is labeled F3. A similar approach is employed for positioning C4 and F4 positions. To obtain the new T5 and T6 positions, a horizontal line which is parallel to the horizontal line between FP1 and FP2 and which intersects the newly labeled PZ position (FZ in standard nomenclature) is created. The T5 position is positioned on that horizontal line at approximately a 3 mm. distance from the PZ position or 67% of the distance between the FP1 and FP2 positions.

The T6 position is selected on the right side following a similar approach. The new P3 position is obtained by dividing the distance between the new T5 position and the new C3 position and placing the P3 electrode half way. A similar approach is employed for obtaining the right frontal position of P4. To obtain the final positions, the halfway point between the new T5 position and the standard F7 position is obtained (for the left frontal area) for the new T3 position and correspondingly on the right hemisphere for the new T4 position.

The digital signals are comparatively analyzed by a computer. The examiner selects from the more than 1000 variables available those which correlate most highly with the categories under consideration. The computer is then programmed to accept the selections and store the digital representations of the signals corresponding to the selected variables. Stepwise regression equations are created by the computer to fit the digitized data developed for each of the classifications. The digital data for fitting the equations is selected by rejecting certain digits or artifacts related directly to data from the FP1 electrode. The FP1 relative value for Delta waves is used. Delta waves are associated with eye movement. The FP1 electrode is positioned above the left eye. This position correlates to eye movements. A split screen monitor showing the subject's face and the delta wave electroencephalograph enables the examiner to note the significance of eye movement to a particular delta wave change.

The computer is programmed to accept variable fixed percentage of the delta wave data up to 45%. The inventor discovered that up to this percentage of data progressively improved the predictive accuracy of the regression equations but that rejecting more than about 45% of the delta wave data deteriorated the predictive accuracy of the regression equations. The regression equations for the four categories are developed based on the known correct responses and then used determine the degree of matching for a series of questions related to an event queried and examined in the same time period or interval. The equations for each of the four categories are used and compared with data obtained during the event under examination and provides an accurate indication of when the subject is likely truthful or likely lying or untruthful when either stating a verbal response or pressing a colored button, green for example, for "yes" or another colored button, red for example, for "no" within a continuous time interval also used to develop the predictor regression equations.

Figures 1, 5B, 5C:
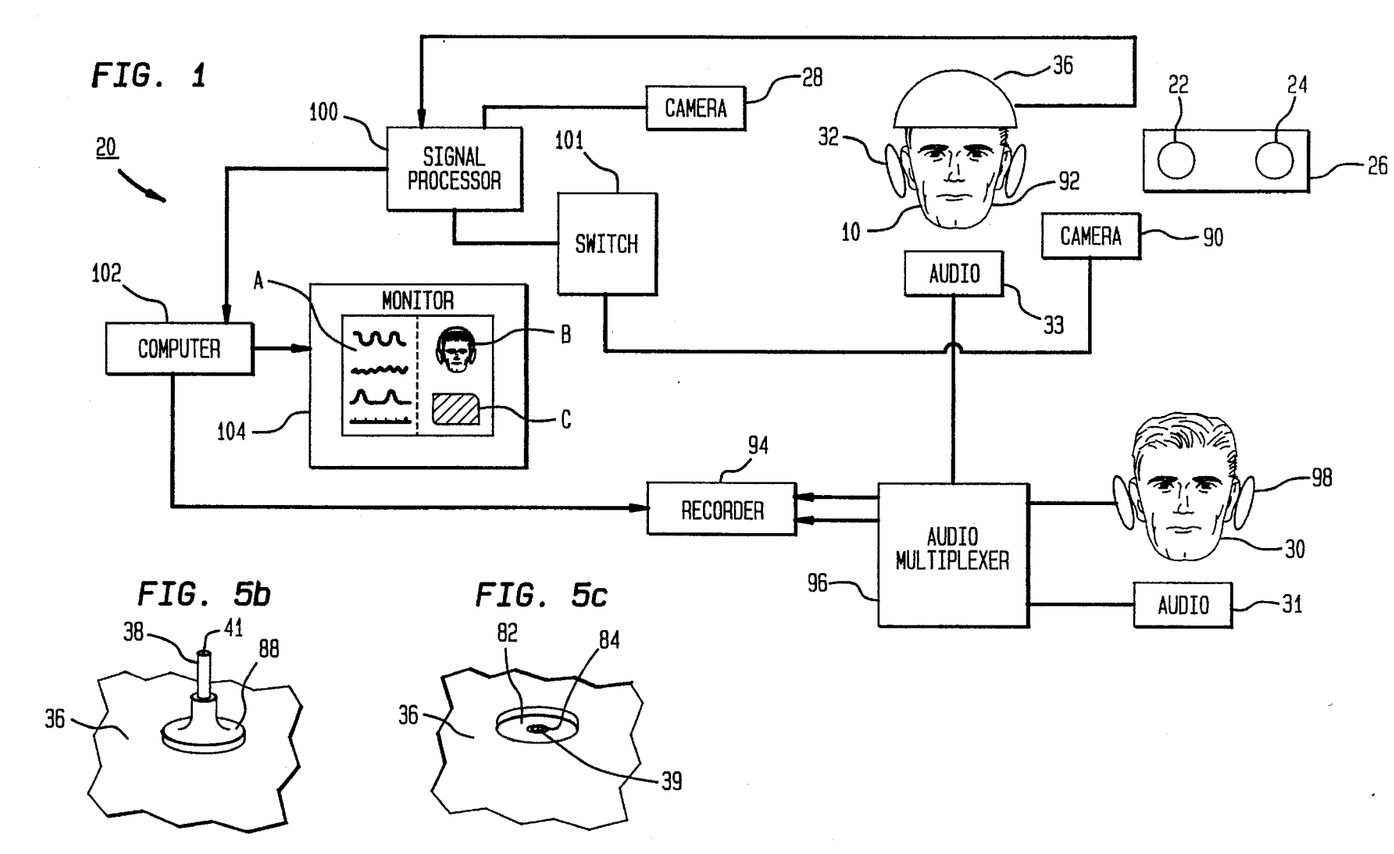
FIG. 1 is a schematic pictorial illustration of the novel apparatus comprising a system utilized to execute the preferred method of the invention.
FIG. 5b is a top perspective view of one of the electrodes mounted in the skull cap.
FIG. 5c is a bottom perspective view of one of the electrodes mounted in the skull cap.

Retorting to FIG. 1 of the drawings, questioning of the subject 10 regarding previous secrets provides a CQT type of procedure in that the control is the subject 10 actually lying and telling the truth regarding a real event. The control questions are thus a true control in the scientific sense. The control questions ("CQ") involve the subject 10 and his or her response when telling the truth and lying. The invention is a substantial improvement over the prior art methodology because it requires accusing the subject of various different crimes and having the regression equations to predict the false crimes during the course of the examination. The operator, examiner or psychologist does not make the predictions using the novel technique.

This invention is an application via the apparatus 20 of the idea that an actuarial approach to decision making is superior to one involving human judgment. The invention extends the use of modem electrophysiological methods by utilizing qualitative electroencephalographic "QEEG" signals in a statistically discriminating method. The prior art's no response period (the before period) and aspects of the push bar response used by Luria are incorporated and extended three orders of magnitude using the novel methodology. The design of the novel apparatus employs a push button response as an option. This approach option requires the subject 10 to push one of two buttons 22 and 24 housed in a box 26. The button 22 is actuated to indicate "yes" and the button 24 is actuated to indicate "no". The indication by the subject 10 is observed and recorded via a video camera 28 for additional comparative analysis with the predictions from the regression equations at the option of the examiner.

For several specimens representing the subject 10, the GKT format was administered by the operator 30. Options were verbally provided to the subject 10, over a microphone 31 via earphones 32, for example. Verbal communication from the subject 10 to the operator 30 was enabled by the microphone 33. An exemplary experiment, method, and the actual results are illustrated below:

Method

Subjects

Four subjects were enlisted as volunteers for the research and were paid for their participation. The subjects were informed of the nature of the design and what would be requested of them during the study.

Apparatus

Figure 2:
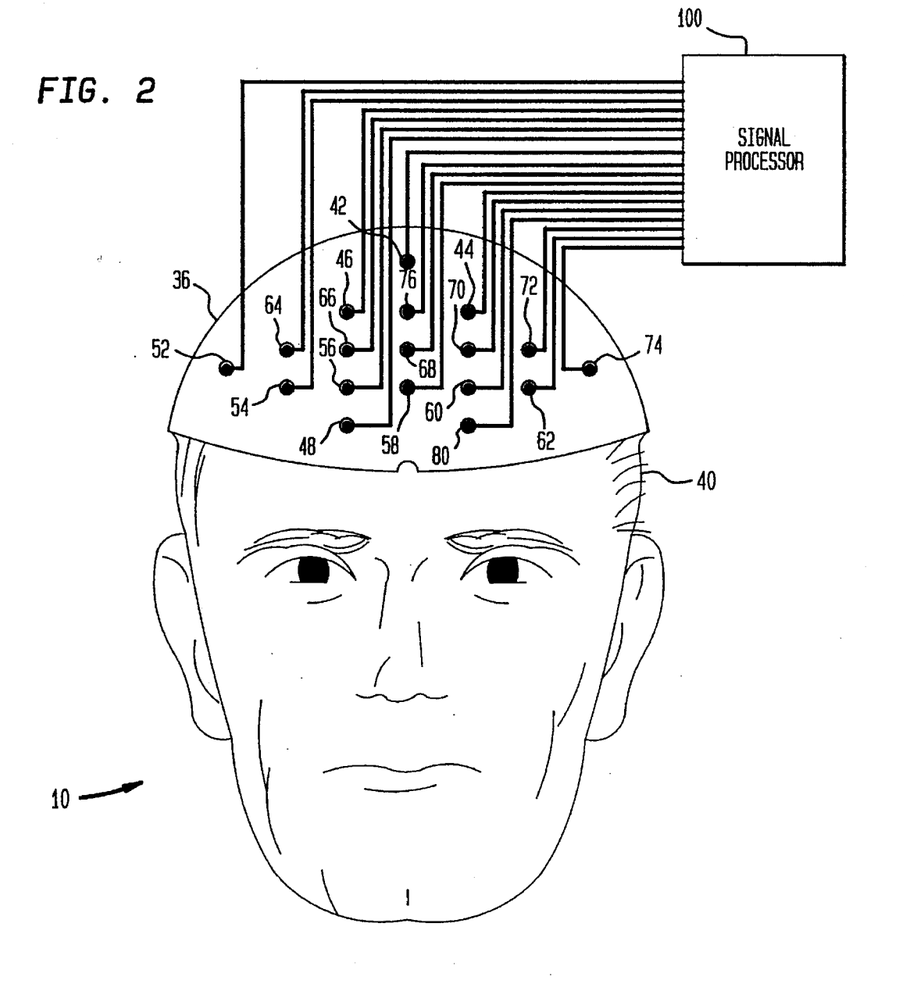
FIG. 2 is a front view of the novel skull cap with electrodes therein and lead lines.

The method, as shown in FIG. 2 involved placing a specially designed cap 36 with recessed hyperdermic needles 38, made of aluminum for example, on the subject's head 40. Sixteen of the hyperdermic needles 38 are located in the head 40 of the subject 10 above and near the frontal lobes of the subject's brain. An electrode assembly 42 is placed in the cap 36 at a location corresponding to the CZ location (central superior) of the brain. Two additional electrodes assemblies 44 and 46 are located in the cap to correspond to the T5 and T6 positions (posterior). Two other electrode assemblies 48 and 50 were located in the cap corresponding to the two standard positions FP1 and FP2.

There is shown in FIG. 2 the assemblies 52, 54, 56, 58, 60 and 62 placed in the cap 36 in locations corresponding to the standard positions F8, F4, C4, FZ, C3, F3, and F7, respectively. Them is also shown the assemblies 64, 66, 68, 70, 72, 74, and 76 pre-placed in the cap 36 in locations selected to correspond to the standard positions T4, P4, GROUND, P3, T3, F7, and PZ.

Figure 3:
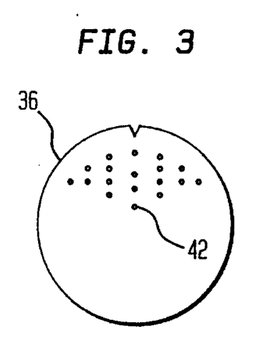
FIG. 3 is a top perspective view of the novel skull cap.
Figure 4:
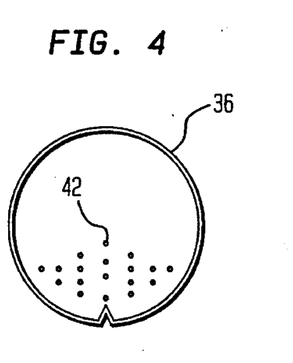
FIG. 4 is a bottom perspective view of the inside of the novel skull cap.

As shown in FIG. 3, the assemblies 42 and 52 thru 76 were employed and positioned, approximately, according to the 10–20 placement system. FIG. 4 shows the inside of the cap 36. The two electrode assemblies 58 and 76 were positioned in the split between the hemispheres in the frontal lobes. The remainder of the electrode assemblies were positioned in the cap 36 and corresponding on the head 40 (FIG. 2) in a geometric fashion to proportionally cover as equally as possible the scalp above the frontal brain lobes (6 left frontal and 6 right frontal).

Figure 5A:
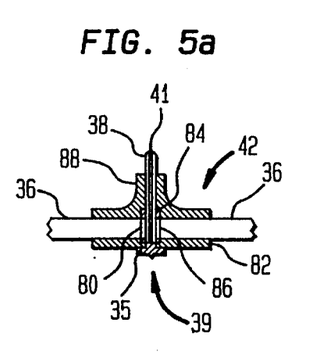
FIG. 5a is a cross-sectional view of the electrode construction in the skull cap.

Shown in FIG. 5a is a cross section of an electrode assembly, for example, assembly 42, mounted in the cap 36 via an aperture 80. A lower fastener 82 has a cylindrical barrel 84, or grommet made of aluminum, for example. The barrel 84 has a cylindrical opening 86 therein adapted to frictionally receive a metal hyperdermic needle 38 and maintain the needle 38 recessed within the barrel 84. The hyperdermic needle 38 resides above the scalp and is hollow having a hole 41 therein adapted to eject a minute amount of a electrically conducting gel 35 into the aperture 39 and the surrounding space to electrically contact the surlhce of the scalp of the subject 92. A female mating upper fastener 88 is adapted to frictionally receive the outside of the barrel 84 as it frictionally engages the lower fastener 82. The fasteners 82 and 88 engage and retain the cap 36. The cap 36 is made of an electrically insulating elastic material, for example vinyl, or a fabric or a like material. The lower fastener 82 and the upper fastener 88 are made of an electrically insulating plastic or Teflon™, for example. In FIG. 5b there is shown a perspective view of the upper fastener 88 surrounding the hyperdermic needle 38 with the hole 41 therein. In FIG. 5c there is shown a perspective view of the lower fastener 82 surrounding the metal cylindrical barrel 84 mounted in the cap 36. The aperture 39 or space into which the gel 35 (shown in FIG. 5a) is extruded is shown.

Procedure

Each subject 10 was asked to provide five stories regarding events in his or her life which the subject 10 would not want anyone else to know about at the time of the testing. This criteria was held to. The QEEG data was recorded at a sampling rate of 256 samples per second. Thus, each epoch equalled a one second period of time. Computer software manufactured by Lexicor Inc. was employed in the recording of the data and software manufactured and available from the Lexicon™ Company was used for generation of the numerical results.

Referring to FIG. 1 again, the QEEG data was recorded simultaneously with dual video recording (one video camera 90 directed at the face 92 of the subject 10 and the other video camera 28 directed towards the answer box 26) and dual audio recording (one audio channel and audio microphone 31 for the examiner 30 and the other audio channel and connected microphone 33 for the subject 10). All five sources of information were recorded via a recorder 94 onto a single 8 MM video tape. The outputs of the microphones 31 and 33 were directed to a audio multiplexer 96 monitored by the examiner 30 via headphones 98, for example. The outputs of the cameras 28 and 90 were fed into a signal processor 100 which also functions as a video mixer for signals from the cameras 28 and 90. The camera 90 is connected to the signal processor 100 via an optional switch 101. An EEG Lexicon™ data collector is incorporated as a component of the signal processor 100 to collect and process signals from the subject's brain.

The subject 10 was asked to respond to all questions with a simple verbal yes or no. Alternatively, the subject 10 was asked to respond by pressing a red button (left button 22) or green button (right button 24) located in the answer box 26 to indicate no or yes, respectively. The subject 10 was asked questions regarding the live events and subsequently the examiner 30 directed the subject 10 to first lie and then to tell the truth regarding those events. The subject 10 was also asked to first lie and then to tell the truth regarding a false crime which the examiner 30 accused the subject 10 of (i.e. running drugs, murdering a hypothetical individual).

Each subject 10 underwent two 15 minutes questioning periods, which resulted in approximately 1000 epochs of data for each period. The system shown in FIG. 1 offers the examiner the option of directing a verbal only response, a push button mechanical response, both types of responses, or a predetermined or random combination of both types of responses.

Data Analysis

Numerical reports were generated from the computer 102 and displayed on the video monitor 104 simultaneously with the outputs from cameras 28 and 90 via software available from Lexicor, Inc. without artifact rejection. Reports were generated for relative power figures of Delta (0–4 Hz), Theta (4–8 Hz), Alpha (8–12 Hz) and Beta1 (12–32 Hz) and Beta2 (32–64 Hz). This resulted in 19 (locations) * 5 (bands) or 95 numbers per second for the relative power figures and recorded by the recorder 94.

Relative power is defined as the total microvolts of a band divided by the total microvolts across all bands. Coherence is defined as the degree of correlation between two points on a particular band width. Phase is a time concept which looks at the time difference between matching sine waves. In addition, coherence and phase relationships were generated via the Lexicor software for all possible relationships of the left and right frontal locations to each other and to the central positions (FZ, PZ,CZ), thus rendering 6 (left frontal)* 8 (left frontal+FZ, CZ, PZ) * 2 (for left frontal and right frontal) * 5 bandwidths or 480 numbers per second for these coherence and phase figures. The positions FP1 and FP2 were not employed in the generation of these numbers, due to their extreme sensitivity to eye movements. In addition, the relationship of the most middle of the left and right frontal positions (arbitrarily defined as P3,P4) to the posterior (T5,T6) positions were analyzed Thus 2*2*5 (bands) or 20 more sets of numbers were generated. In addition, the peak amplitude and peak frequency of each of the bands were generated for each location (thus 19(locations)*5(bands)*2(measures) or 190 additional sets of numbers per second). Ratio symmetry measures (of the bands) for the left frontal area (3 positions) were also employed as preliminary research had indicated that this was an important area in the differentiation of the lie/truth distinction. The Lexicor software defines the ratio symmetry measure as A/B with B being the larger of the two numbers. Ratio symmetry measures were also taken for all positions relative to their homologous positions on the opposite hemispheres. Thus 8 (left hemisphere) * 5 (bands) or 40 additional sets of numbers plus the left frontal symmetry measures of 3(locations)*2(locations)*5(bands) or 30 numbers. The following represents the total number of figures generated per second of data by the measures employed.

| Measure | Relationships | Numbers |
| --- | --- | --- |
| Relative Power | 19 (locations) * 5 (bands) | 90 |
| (an additional number for total microvolts was also generated) | | 19 |
| Coherence | | |
| | Left Frontal | |
| | 6 (left frontal) * 5(left frontal) * 5 (bands) | 150 |
| | 6 (left frontal) * 3 (fz,pz,cz) * 5(bands) | 90 |
| | Right Frontal | |
| | 6 (right frontal) * 5(right frontal) * 5 (bands) | 150 |
| | 6 (right frontal) * 3 (fz,pz,cz) * 5(bands) | 90 |
| Phase | similar to coherence | 480 |
| Frontal Relationship to Posterior in terms of Coherence and Phase | | |
| 2 central positions(left and right frontal) * 2 posterior positions (T5,T6)*5(bands)* 2 measures(coherence and phase) | | 40 |
| Symmetry Measures | | |
| Hemisphere | 8 left hemisphere vs. right hemisphere homologous locations* 5 bandwidths | 40 |
| Left Frontal | 3 (locations) * 2 (locations) * 5 (bands) | 30 |
| Peak Amplitude | 19 (locations) * 5 bands | 90 |
| Peak Frequency | 19 (locations) * 5 bands | 90 |
| | TOTAL | 1359 |

Thus, for a 15 minute period of time a total of 60(seconds) * 15 (minutes) * 1359 (numbers per second) or 1,223,100 actuarial numbers are generated.

The numerical data generated and collected make up four subsets $E_1$, $E_2$, $E_3$, and $E_4$. These four subsets constitute the before-lie versus before-truth numerical continuums. The regression equations differentiate known before-lie versus known before-truth and known during-truth versus known during-lie numerical continuums. Thus, two equations are developed from the digital numbers, and likewise two equations are also developed from logarithms of these digital numbers. Using the cutoff approach, these cutoff numbers are employed when the regression equations predict to the yet unlabeled (but known to the examiner) events (i.e., before-truth versus before-lie, and during-truth versus during-lie). Thereafter, each predicted-to epoch is labeled according to whether it was predicted to be a truth or a lie (i.e., during or before) for both the digital numbers and their logarithms. These classifications are then compared to the reality of the statement (known to the examiner) and the respective accuracy is examined. A further cut-off is employed. Predicted-to epochs can fall into three categories (i.e., true, false, and "unable to predict"). The true and false categories are counted up for each event (e.g., a crime). A cut-off is then employed to determine the accuracy of the prediction. Thus, for a particular event, there may be 40 epochs, for example, which may be predicted as to the truth or falsity of the subject's response. If a certain percentage of those responses indicate that the subject is innocent of the crime (i.e., the event), then the novel system indicates that the subject is innocent (i.e., has no knowledge of the crime or event) or vice-versa.

The video tape created by the recorder 94 was analyzed by the examiner 30 and each relevant epoch was categorized as to whether it preceded a lie or truth (during which the examiner 30 was asking the questions) or was during the period when the subject 10 was telling the truth or lying. Epochs were thus labeled as before a lie, before a truth, during a lie and during the truth. For each subject 10, all of the real events and false accusations were labeled in such a manner.

The labels for at least three of the real events and at least one of the false crimes (depending upon how many false accusations were presented) were placed in a separate column in a spreadsheet. The spreadsheet data was then employed to generate a stepwise multiple regression equation.

All of the data was grouped into several different spreadsheets employing Excel 5. One spreadsheet was not sufficient to hold the data and transfer it to a software multiple regression program such as that provided by CSS Statistica, for example. The spreadsheets are presently confined to approximately 250 columns.

Statsoft™ software available from CSS Statistica was employed to analyze the data and discover the variables which had the highest correlation with the categorical variables of before lie/before truth and lie/truth. The variables which were unable to aid in differentiating the difference between the four classes of events were discarded. The correlations were generated under a selection condition which analyzed only the data for which the FP1 relative delta power was under a certain figure (e.g. a figure in the range from 30 to 45). The modification of the method so as to use this cut off in both the initial selection of variables and again in the final analysis is related to correlation of the effect of eye movements on the relative power of delta figure in the frontal lobes of the brain.

Eye movements produce a large amount of delta, and thus normally are considered artifactual. However, in this novel method, what is normally considered by the prior an to be artifacts are as much a part of the prediction problem as other brain signals. For example, for some cases, the subject 10 when lying may be more likely to wink or initiate eye movements.

It has been discovered that the examiner 30 should limit or place a restriction on the amount of relative delta and that this restriction causes at least 25% of the delta wave data to be discarded. By employing this criteria, effectiveness of the resulting regression equations is substantially improved. If no restriction is in place, then there is generally no distinct correlation between the data and the categories under investigation. Thus, artifact control by elimination of the relative delta figures above a certain amount allowed for some control of gross artifacts (though not eliminating all of them) and substantially improved the accuracy of the prediction by the equations.

The variables were selected in the above manner until there were approximately under 100 variables which maintained high correlations (for example, from 0.20 to 0.70) to the prediction categories. These variables were then transformed to logarithmic numbers (base 10) employing the Excel spreadsheet and both sets of numbers placed into one spreadsheet and transferred to the CSS Statistica format.

The CSS Statistica stepwise multiple regression software was employed to develop equations for both the before and during conditions for the base three real events and base one or two false accusation events combined. Only the epochs for which the subject 10 indicated non-involvement in the false crime (i.e. telling the truth regarding innocence) were employed in generating the regression equations.

Analysis of the data indicated that when one is admitting to a crime that one did not commit, the brain's overall state is different than when one is lying about a real event which took place. This difference reduced significantly the sensitivity of the regression equations. Since the lie detection problem is relevant in the situation of determining if an individual did or did not commit a crime, the usefulness of false admissions is not relevant.

In the generation of the initial equations, using a cut-off of 45% for the delta relative power figures provided an acceptable figure of predictability for the original data. This figure would generally be above a 0.98 or 1.00 figure.

Separate regression equations were developed for the original data (correlations, peak frequency numbers, etc) and the logarithmic numbers for both the before and during conditions (4 equations per subject per session).

Several methods of obtaining the data are provided by the novel system. Two methods involve 1) the subject verbally answering yes or no and 2) the subject pressing a red or green button indicating yes or no. The initial equations can be developed with both conditions being the base line.

The regression equations were analyzed according to their hit rate on the base conditions. The CSS Statistica software was used to label the epochs/rows with numbers, thus a before lie epoch is labeled 100, the lie epoch 101, the before truth epoch 102 and the truth epoch 103. The numbers vary according to what epoch is analyzed first, second, etc. Regression results were presented graphically in terms of where an epoch resides in a truth-falsity continuum. Thus, a particular epoch may be numbered as 101.354, thus residing somewhere between a before lie and before truth rating. The regression equations were developed only on two conditions at a time, either the before condition or during condition.

The results of the regression equations for the base line condition were visually analyzed and a cut off range established such that there would be no false positives and no false negatives for the base conditions. Thus, a range of 100.5 to 101.5 is a possible result which indicates an overlap range where before truth epochs can overlap with before lie epochs.

Figure 6:
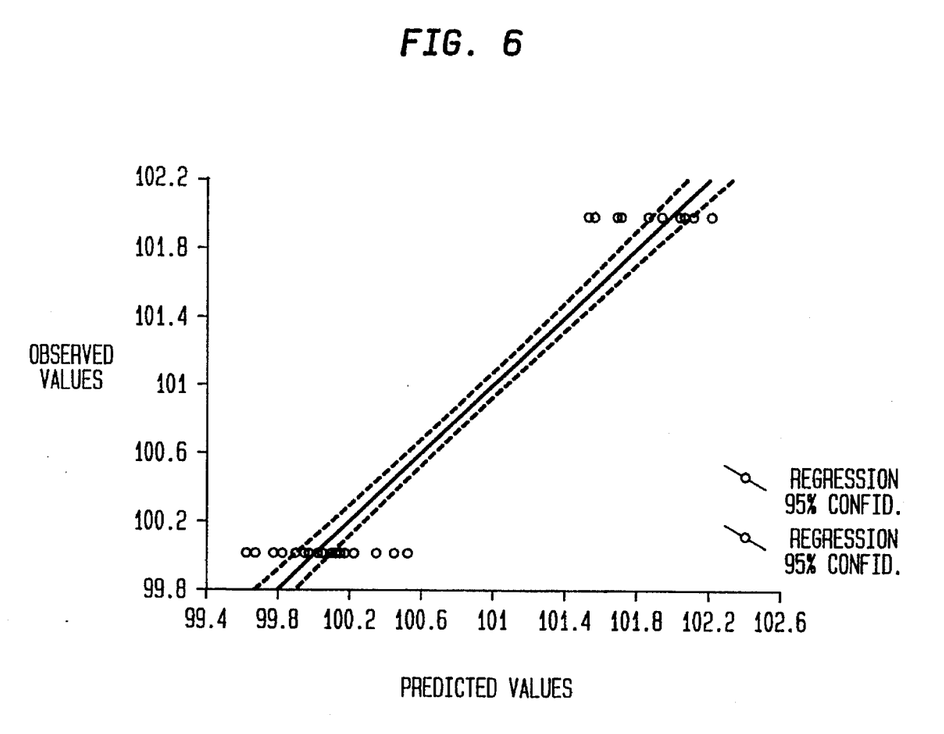
FIG. 6 is a graph illustrating predicted values versus observed values using regression equations created by the novel method.

On some of the regression equations, there is no overlap of prediction results, but a large gap. In these conditions, only the upper and lower range of the accurate hits are employed. The cut off issue is presented graphically in FIG. 6. This approach ensures the highest accuracy. Thus, no epoch is labeled unless the original regression equation unequivocally places that value in the correct category.

It is foreseeable by the inventor that as the adhesive-solubility-conductivity properties of conductive pastes improve the conductive pin described herein may be replaced by flattened metallic surfaces combined with these improved conductive pastes for use in place of the conducting pins or needles described herein.

It is within the scope of this invention and one skilled in this art may adapt the system disclosed herein to make other types of determinations.

Thus, it can be seen from the foregoing description of the currently preferred fabricated and working embodiment and the following claims that a new and useful method, electrode cap, and system have been illustrated and described and that modifications, equivalents and changes can be made therein by persons of ordinary skill without departing from either the scope of the claims or the spirit of the novel invention.

What is claimed is:

1. A disposable cap comprising a hemispherically shaped member adapted to fit on top of a human head, the hemispherically shaped member having an exterior and an interior and further having at least nineteen electrically conducting electrodes pre-placed therein at specific positions, each of the electrodes being adapted with a metal conducting object extending through the exterior of the member for transmitting electroencephalographic signals from the human brain for analysis, the member being made of an insulating material, the member having an anterior portion divided into a left dorsal area and a right dorsal area, the member also having a posterior portion, the posterior portion having dispersed therein at least nineteen of the electrodes, said electrodes extending from the interior of the member to the exterior, means for holding said electrodes in said member, said electrodes being non-standardly arranged at positions C3, C4, F3, F4, F7, F8, FP2, FP1, P3, P4, T3, T4, T5, T6, PZ, CZ, FZ and ground, a set of fourteen of the eighteen electrodes, comprised of first and second subsets of seven electrodes each being located in the member, said set of fourteen being equally divided and dispersed in mirror-image positions in the anterior portion of the member, the first subset of seven of the electrodes being located in the left dorsal area of the member at the T4, T6, P4, F4, C4, F8, and FP2 positions, the second subset of seven of the electrodes being located in mirror image positions with respect to the first subset in the right dorsal area of the member at the T3, T5, P3, F3, C3, F3, and FP1 positions, respectively, one other of the electrodes being ground and centrally located between the right and left dorsal areas, and two additional electrodes also being centrally located between the right and left dorsal areas, wherein one is located above the ground electrode at the PZ position and wherein the other one is located below the ground electrode at the FZ position.

2. The cap according to claim 1 wherein the electrodes corresponding to the positions FP2 and FP1 are located in a first horizontal plane and spaced approximately 4 to 5 millimeters apart; the electrodes corresponding to the positions F8, F4,C4, FZ, C3, F3, and F7 are spaced apart and located in a second horizontal plane above said first horizontal plane; the electrodes corresponding to the positions T4, P4, ground, P3, and T3 are spaced apart and located in a third horizontal plane above said second horizontal plane; the electrodes corresponding to the T6 and T5 positions are spaced approximately 6 millimeters apart and located in a fourth horizontal plane above said third horizontal plane; and wherein said electrode corresponding to the position PZ is centrally located between the T5 and T6 positions; and wherein the electrodes corresponding to the positions CZ, PZ and FZ are located in a vertical plane wherein lies the ground electrode between the PZ and FZ positions, the PZ and FZ positions being separated by approximately 4 to 5 millimeters.

3. The cap according to claim 2 wherein the hemispherically shaped member is flexible.

4. The cap according to claim 3 wherein the hemispherically shaped member is elastic.

5. An actuarial method for a statistical determination of whether a cognitive response of a human subject having right and left frontal lobes comprising a brain underneath a scalp, to a question selected from a plurality of questions is either true, false, made before a true statement, or made before a false statement based on prior acquisition and statistical analysis of quantitative aspects of electroencephalographic responses to known events by the subject comprising:

(a) detachably affixing at least nineteen electrodes, to the scalp of the subject where the scalp overlies the frontal lobes of the subject's brain said electrodes being nonstandardly arranged at positions C3, C4, F3, F4, F7, F5, FP2, FP1, P3, P4, T3, T4, T5, T6, PZ, CZ, FZ and gound, a set of fourteen of the nineteen electrodes, comprised of first and second subsets of seven electrodes each being located on the scalp, said set of fourteen being equally divided and dispersed in mirror-image positions in an anterior portion of the scalp, the first subset of seven of the electrodes being located in a left dorsal area of the scalp at the T4, T6, P4, F4, C4, F8, and FP2 positions, the second subset of seven of the electrodes being located in mirror-image positions with respect to the first subset in a right dorsal area of the scalp at the T3, T5, P3, F3, C3, F3, and FP1 positions, respectively, one other of the electrodes being, a ground electrode and centrally located between the right and left dorsal areas, and two additional electrodes also being centrally located between the fight and left dorsal areas, wherein the one additional electrode is located above the ground electrode at the PZ position and wherein the other additional electrode is located below the ground electrode at the FZ position, one of said electrodes being located above a left eye of the subject in the FP1 position and another of said electrodes being located above a right eye of the subject in the FP2 position;

(b) measuring, using said electrodes all evenly located above the frontal lobes of the brain, a relative power of a brain wave activity at one electrode compared to another electrode of the subject via a voltage at the one electrode compared to the voltage at other said electrodes, the brain wave activity comprising at least 95 different relative power voltage versus time analog measurements while the subject responds to a plurality of false events and true events over a predetermined first time interval and rejecting epochs on a basis, said basis comprising comparing relative power of a delta wave input from the electrode in the FP1 position:

(c) converting the analog measurements to a plurality N of digital numbers wherein each number represents a measure of a voltage signal from each of the at least nineteen electrodes at a specific time-point in the first time interval;

(d) converting each of the plurality N of digital numbers to a base 10 logarithmic equivalent to obtain a corresponding plurality $N_L$ of logarithmic numbers;

(e) identifying a plurality of epochs within the first time interval; and then categorizing each epoch into one of four event spectra in the time interval, the spectra being identified as (i) a first spectrum comprising epochs during a query directed to the subject by the examiner about a known statement of a truth, (ii) a second spectrum comprising epochs occurring during a known statement of a lie by the subject, (iii) a third spectrum comprising epochs occurring before a known statement of a lie by the subject, and (iv) a fourth spectrum comprising epochs occurring before a truth by the subject;

(f) selecting four subsets $E_1$, $E_2$, $E_3$, and $E_4$ from the plurality of logarithmic numbers $N_L$, the four subsets $E_1$, $E_2$, $E_3$, and $E_4$ being grouped in time-related subsets consisting of epochs wherein each epoch of each subset is selected from one and only one of said four event spectra, respectively, (g) computing a first equation consisting of a first stepwise regression equation using a portion of the digital numbers N corresponding to the subset $E_1+E_2$ of logarithmic numbers $N_L$ from said first spectrum and said second spectrum;

(h) computing a second equation consisting of a second stepwise regression equation using a portion of the digital numbers N corresponding to the subset $E_3+E_4$ of logarithmic numbers $N_L$ from said third and fourth spectrums;

(i) computing a third equation consisting of a third stepwise regression equation using a portion of the digital numbers N corresponding to the subset $E_1+E_2$ of logarithmic numbers $N_L$ from said first and $E_4$ third spectrums;

(j) computing a fourth equation consisting of a fourth stepwise regression equation using a portion of the digital numbers N corresponding to the subset $E_3+E_4$ of logarithmic numbers $N_L$ from said third and fourth spectrums;

(k) further examining the subject regarding a subject within said time interval with questions and each question requiring an examination answer;

(l) measuring the brain wave activity of the subject via said electrodes as voltage versus time analog measurements while the subject verbally answers the questions;

(m) convening the analog measurements taken during the examination to a plurality M of digital numbers wherein each number represents the relative amplitude of the voltage signal from each electrode at a specific point during the examination of the subject;

(n) converting the plurality M of digital numbers to their base 10 logarithmic equivalent to obtain a like plurality of logarithmic numbers $M_E$;

(o) selecting for examination a plurality of examination epochs and a corresponding subset of numbers from the logarithmic numbers $M_E$ generated from within said time interval based on at least one examination response provided by the subject;

(p) comparing the plurality of logarithmic numbers $M_E$ and the plurality of digital numbers M with predicted values provided by said first, second, third, and fourth equations;

(q) selecting as a spectrum for the compared plurality of logarithmic numbers $M_E$ that spectrum associated with predicted values from one of said equations which substantially matches the compared plurality of logarithmic numbers $M_E$; and then (q) indicating that the response provided by the subject during the selected plurality of examination epochs is either before a true statement, during a true statement, before a lie, or during a lie based on the spectrum last selected.

6. The method of claim 5 wherein each examination epoch is represented by a numerically sequential plurality of logarithmic numbers $M_E$.

7. A method of determining whether a cognitive response, of a human subject having a plurality of frontal lobes comprising a brain underneath a scalp, to a question selected from a plurality of questions is true or false comprising:

(a) attaching at least nineteen electrodes to the scalp of the subject where the scalp overlies the frontal lobes of the subject's brain, said electrodes being non-standardly arranged at positions C3, C4, F3, F4, F7, F8, FP2, FP1, P3, P4, T3, T4, T5, T6, PZ, CZ, FZ and ground, a set of fourteen of the nineteen electrodes, comprised of first and second subsets of seven electrodes each being located on the scalp, said set of fourteen being equally divided and dispersed in mirror-image positions in an anterior portion of the scalp, the first subset of seven of the electrodes being located in a left dorsal area of the scalp at the T4, T6, P4, F4, C4, F8, and FP2 positions, the second subset of sewn of the electrodes being located in mirror-image positions with respect to the first subset in a right dorsal area of the scalp at the T3, T5, P3, F3, C3, F3, and FP1 positions, respectively, one other of the electrodes being a ground electrode and centrally located between the right and left dorsal areas, and two additional electrodes also being centrally located between the right and left dorsal areas, wherein one of the additional electrodes is located above the ground electrode at the PZ position and wherein the other additional electrode is located below the ground electrode at the FZ position, one of said electrodes being located above a left eye of the subject in an FP1 position and another of said electrodes being located above a right eye of the subject in an FP2 position;

(b) measuring a brain wave activity of the subject via said electrodes as voltage versus time analog measurements while the subject verbally describes a plurality of false events and true events over a time interval and rejecting epochs on a basis, said basis comprising determining a relative power of delta waves from the FP1 position;

(c) converting the analog measurements to a plurality N of digital numbers wherein each number represents a relative amplitude of a voltage signal from each of at least eighteen electrodes compared to at least two electrically interconnected reference electrodes connected to each ear, at a specific time-point in the time interval;

(d) converting the plurality N of digital numbers to their base 10 logarithmic equivalent to obtain a like plurality of logarithmic numbers $N_L$;

(e) identifying a plurality of epochs within the time interval; and then categorizing each epoch into one of four event spectra in the time interval, the spectra being identified as (i) a first spectrum comprising numbers occurring before a known statement of a truth by the subject, (ii) a second spectrum comprising numbers occurring during a known statement of a lie by the subject, (iii) a third spectrum comprising numbers occurring before a known statement of the lie by the subject, and (iv) a fourth spectrum comprising numbers occurring during a known statement of the truth by the subject;

(f) selecting four subsets $E_1$, $E_2$, $E_3$, and $E_4$ from the plurality of logarithmic numbers $N_L$, the four subsets $E_1$, $E_2$, $E_3$, and $E_4$ being grouped in time-related subsets which relate directly to said four event spectra, respectively;

(g) computing a first equation consisting of a before-lie stepwise regression equation using a portion of the subsets $E_1$ and $E_3$ of logarithmic numbers $N_L$ from said first and third spectrums;

(h) computing a second equation consisting of a during-lie stepwise regression equation using a portion of the subsets $E_2$ and $E_4$ of logarithmic numbers $N_L$ from said second and fourth spectrums;

(i) computing a third equation consisting of a before-truth stepwise regression equation using a portion of the subsets $E_1$ and $E_3$ of digital numbers $N_L$ from said first and third spectrums and computing a fourth equation consisting of a during-truth stepwise regression equation using a portion of the subset $E_2$ and $E_4$ of digital numbers $N_L$ from said second and fourth spectrums;

(j) examining the subject in an examination regarding other subject matter within the time interval with at least one question and requiring an answer to said question;

(k) measuring the brain wave activity of the subject via said electrodes as voltage versus time analog measurements while the subject verbally answers at least the one question;

(l) converting the analog measurements taken during said examination to a plurality M of digital numbers wherein each number represents the relative amplitude of the voltage signal from each electrode at a specific point during the examination of the subject;

(m) convening the plurality M of digital numbers to their base 10 logarithmic equivalent to obtain a like plurality of logarithmic numbers $M_E$;

(n) correlating the plurality of logarithmic numbers $M_E$ to the time spectra corresponding to the at least one said answer provided by the subject during said examination;

(o) comparing the plurality of logarithmic numbers $M_E$ and the plurality of digital numbers M related to the time spectra for the answers provided by the subject with a plurality of predicted values provided by the first, second, third, and fourth equations;

(p) selecting a series of examination epochs from said time interval and representing said series by the plurality of logarithmic numbers $M_E$ occurring therein, each of the logarithmic number $M_E$ having an actual value;

(q) testing each said answer provided by the subject during said series by a quantitatively numerical comparison of the actual values of the plurality of logarithmic numbers $M_E$ representing the series the plurality of predicted values by the first, second, third, or fourth equations, respectively; p1 (r) indicating that the response provided by the subject during said examination epoch is true upon concurrence of the following:

(1) The actual values of the plurality of logarithmic numbers $M_E$ occurring during said series substantially match approximately 95% of the values predicted by the first and second equations; and (2) The actual values of a plurality of digital numbers M occurring during said series substantially match approximately 95% of the values predicted by the third and fourth equations.

8. The method of claim 7 wherein said series is represented by a numerically sequential plurality of logarithmic numbers $M_E$.

9. A system for determining whether a statement made by a subject is true or false by questioning during an examination comprising:

(a) A central processing unit;

(b) a video monitor connected to the central processing unit;

(c) a video recorder and an audio recorder connected to the central processing unit;

(d) means for communicating verbal instructions and a question to the subject from an examiner connected to said audio recorder, said audio recorder being interconnected to the central processing unit;

(e) means for the examiner to receive a responsive answer from the subject connected to said audio recorder, said recorders being interconnected to the central processing unit;

(f) means for displaying a real time video image of the subject on a first part of the monitor interconnected to the central processing unit;

(g) means for electrically conductively attaching at least eighteen electrodes to a scalp of the subject where the scalp overlies a pair of frontal lobes of the subject's brain, said electrodes being non-standardly arranged at positions C3, C4, F3, F4, F7, F8, FP2, FP1, P3, P4, T3, T4, T5, T6, PZ, CZ, FZ and ground, a set of fourteen of the nineteen electrodes, comprised of first and second subsets of seven electrodes each being located on the scalp, said set of fourteen being equally divided and dispersed in mirror-image positions in an anterior portion of the scalp, the first subset of seven of the electrodes being located in a left dorsal area of the scalp at the scalp T4, T6, P4, F4, C4, F8, and FP2 positions, the second subset of seven of the electrodes being located in mirror-image positions with respect to the first subset in a right dorsal area of the scalp at the T3, T5, P3, F3, C3, F3, and FP1 positions, respectively, one other of the electrodes being a ground electrode and centrally located between the right and left dorsal areas, and two additional electrodes also being centrally located between the right and left dorsal areas, wherein one is located above the ground electrode at the PZ position and wherein the other one is located below the ground electrode at the FZ position, one of said electrodes being located above a left eye of the subject in the FP1 position and another of said electrodes being located above a right eye of the subject in the FP2 position interconnected to the central processing unit;

(h) means for measuring a brain wave activity of the subject via said electrodes as voltage versus time analog measurements, while the subject verbally describes a plurality of false events and true events within a predetermined time interval, interconnected to the central processing unit, and means for selectively rejecting some measurements based upon a relative power of the delta wave signals from the electrode in the FP1 position and the electrode in the FP2 position interconnected to the central processing unit;

(i) means fix displaying said analog voltage measurements on a second portion of said monitor simultaneously with the image of the subject interconnected to the central processing unit;

(j) means for converting the analog measurements to a plurality N of digital numbers, wherein each number represents the relative amplitude of the voltage signal from each of seventeen electrodes selected from the at least eighteen electrodes compared to a centrally located ground electrode at a specific point in time within said time interval, interconnected to the central processing unit; said system further comprising, (k) first computer means for converting the plurality N of digital numbers to their base 10 logarithmic equivalent to obtain a like plurality of logarithmic numbers $N_L$;

(l) second computer means for identifying a plurality of epochs within the time interval; and then categorizing each epoch into one of four event spectra in said time interval, the spectra being identified to the second computer means as (i) a first spectrum comprising occurring before a known statement of a truth by the subject, (ii) a second spectrum comprising occurring during a known statement of a lie by the subject, (iii) a third spectrum comprising occurring before a known statement of the lie by the subject, and (iv) a fourth spectrum comprising occurring during a known statement of the truth by the subject;

(m) third computer means for selecting four subsets $E_1$, $E_2$, $E_3$, and $E_4$ from the plurality of logarithmic numbers $N_L$, the four subsets $E_1$, $E_2$, $E_3$, and $E_4$ being grouped in time-related subsets which relate directly to said four event spectra, respectively;

(n) fourth computer means for computing a first equation consisting of a before-lie versus before-truth stepwise regression equation using at least a portion of the subset $E_1$ of logarithmic numbers $N_L$ from said first spectrum;

(o) fifth computer means for computing a second equation consisting of a during-lie versus during-truth stepwise regression equation using at least a portion of the subset $E_2$ of logarithmic numbers $N_L$ from said second spectrum;

(p) sixth computer means for computing a third equation consisting of a before-truth versus before-lie stepwise regression equation using at least a portion of the subset $E_3$ of logarithmic numbers $N_L$ from said third spectrum;

(q) seventh computer means for computing a fourth equation consisting of a during-truth versus during-lie stepwise regression equation using at least a portion of the subset $E_4$ of logarithmic numbers $N_L$ from said fourth spectrum;

(r) a recording means connected to audio multiplexer connected to a first microphone adapted to transmit verbal responses from the subject, the audio multiplexer also being connected to a second microphone adapted for verbally examining the subject via said means for communicating verbal instructions and at least one question to the subject from the examiner and requiring an answer within said predetermined time interval, said recording means recording from said microphone and said means for communicating verbal instructions;

(s) signal processor means for digitizing the measurements of brain wave activity of the subject via said electrodes as voltage versus time analog measurements while the subject verbally answers the questions into discrete numbers corresponding to specific points in said time interval;

(t) eighth computer means for converting the analog measurements taken during said examination to a plurality M of digital numbers wherein each number represents the relative amplitude of the voltage signal from each electrode at a specific point during said examination of the subject;

(u) ninth computer means for convening the plurality M of digital numbers to their base 10 logarithmic equivalent to obtain a like plurality of logarithmic numbers $M_E$;

(v) tenth computer means for correlating the plurality of logarithmic numbers $M_E$ to the time spectra corresponding to an answer provided by the subject during said examination;

(w) eleventh computer means for comparing the plurality of logarithmic numbers $M_E$ related to the time spectra for said answer provided by the subject with the predicted values provided by the first, second, third, and fourth equations;

(x) twelfth computer means for storing a selected series of epochs from said time interval and representing said series by the plurality of logarithmic numbers $M_E$ occurring therein;

(y) thirteenth computer means for quantitatively numerically comparing data arising in the course of said answer provided by the subject during the selected series by a numerical comparison of the actual values of at least a portion of the plurality of logarithmic numbers $M_E$ with the values predicted by the first, second, third, or fourth equation, respectively;

(z) indicator means for indicating that said answer provided by the subject is either true or false connected to a fourteenth computer means for calculating a concurrence of the following:

(1) That at least a portion of actual values of the plurality of logarithmic numbers $\dot{M}_E$ occurring during the selected series substantially match approximately 95% of the values predicted by the third equation; and (2) That at least a portion of the actual values of a plurality of logarithmic numbers $M_E$ occurring during said series selected from epochs preceding said answer substantially match at least 95% of the values predicted by the first equation, said system further comprising:

Said first, second, third, fourth, fifth, sixth, seventh, eighth, ninth, tenth, eleventh, twelfth, thirteenth, and fourteen computer means being integrated into said central processing unit, said central processing unit being adapted to receive digital signals from said signal processor, said central processing unit being further adapted to direct first digital signals representing what is shown on the first portion of said monitor to said video recorder, said central processing unit being further adapted to direct second digital signals representing an image of said subject to said video recorder, and said central processing unit being further adapted to direct third digital signals representing the image displayed on the third portion of said monitor to said video recorder.

10. The system according to claim 9 wherein said means for the examiner to receive responsive answers from the subject comprises a "yes or no" answer box having a first manually actable means and a second actable means physically distinguishable from said manually actable means, displaying means for displaying a video image of said first and second actable means, said displaying means further comprising means for indicating the actuation chosen by the subject.

11. The system according to claim 9 wherein said mean for the examiner to receive responsive answers from the subject comprises manual means for manually signalling a response by the subject to a question from the examiner comprising a pair of individually distinctive depressable buttons and means for displaying said manual means on a third portion of said monitor simultaneously with said image of the subject and said analog measurements.

12. The system according to claim 11 wherein said means for the examiner to receive responsive answers from the subject comprises means for conveying an audio signal from the subject to the examiner interconnected to a microphone adapted to convey communications from the subject.

\* \* \* \* \*